United States Patent [19]

Bockelmann

[11] 4,212,397
[45] Jul. 15, 1980

[54] SEPARATION OF MATERIALS

[76] Inventor: Manfred Bockelmann, 65 Maid Marion Ave., Robindale, Transvaal, South Africa

[21] Appl. No.: 745,896

[22] Filed: Nov. 29, 1976

[30] Foreign Application Priority Data

Dec. 8, 1975 [ZA] South Africa ............... 75/7668

[51] Int. Cl.² ................. B07C 5/346; G01J 1/58
[52] U.S. Cl. ......................... 209/589; 209/576; 250/459
[58] Field of Search ............ 209/111.5, 563, 564, 209/566, 571, 576, 577, 578, 587, 589; 250/460, 458, 459, 361 R, 362, 363, 365, 461 R

[56] References Cited

U.S. PATENT DOCUMENTS

| Re. 25,320 | 1/1963 | Lewis et al. ............ 250/461 R X |
| 2,890,347 | 6/1959 | McCormick ............ 209/111.5 X |
| 3,011,634 | 12/1961 | Hutter et al. ............ 209/111.5 X |
| 3,137,392 | 6/1964 | Slight .................... 209/111.5 |
| 3,390,268 | 6/1968 | Witte et al. ............ 250/365 |
| 3,650,400 | 3/1972 | Warren et al. ............ 209/111.5 |
| 3,917,947 | 11/1975 | Fenton .................. 209/111.5 X |
| 4,018,530 | 4/1977 | Hirschfeld ............ 250/459 X |

FOREIGN PATENT DOCUMENTS

| 1155088 | 6/1969 | United Kingdom .............. 250/460 |
| 161703 | 4/1964 | U.S.S.R. ...................... 209/111.5 |

OTHER PUBLICATIONS

*IBM Technical Disclosure Bulletin*, vol. 8, No. 7, Dec. 1965, p. 983.

*Primary Examiner*—Joseph J. Rolla
*Assistant Examiner*—Edward M. Wacyra
*Attorney, Agent, or Firm*—Beveridge, DeGrandi, Kline & Lunsford

[57] ABSTRACT

Apparatus for separating a selected material from a batch of particulate material in which a stream of the particulate material is irradiated with pulsed electromagnetic radiation such as X-rays to cause the selected material to fluoresce. The fluorescing material is then detected and ejected from the stream.

7 Claims, 4 Drawing Figures

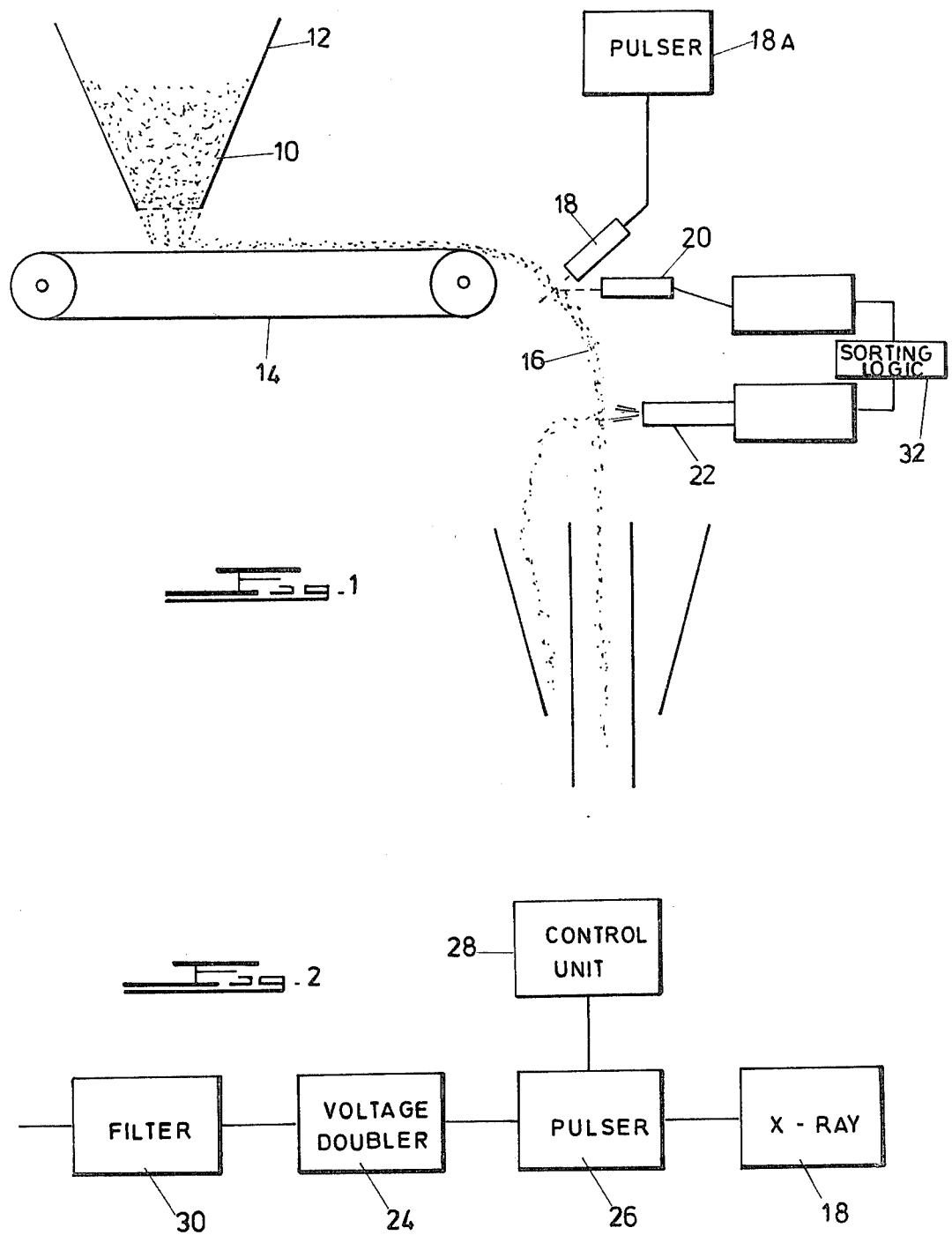

SEPARATION OF MATERIALS

This invention relates to the separation of materials. More particularly but not exclusively it relates to the separation of diamonds from diamondiferous material.

In a known method of separating diamonds from diamondiferous material the material is deposited on an endless conveyor belt. At the forward end of the upper bight of the belt the material is discharged therefrom in a continuous stream. The falling stream of material is irradiated with continuous X-rays from an X-ray tube which causes the diamonds in the stream to fluoresce. A suitable detector, such as a photomultiplier tube, is then located downstream of the X-ray tube to detect the fluorescing diamonds in the stream. The output of the detector is arranged to control a compressed air nozzle to deflect the fluorescing diamonds from the stream.

Whilst the abovementioned method is satisfactory in many respects it does have certain important drawbacks. Firstly, its electrical power requirement is of the order of 1000 Watts. This means that special cooling facilities (normally water cooling) have to be provided on the X-ray rube which in turn means that the equipment becomes expensive and heavy. It also means that a separate power supply usually has to be provided which entails power cables and their resulting disadvantages. Secondly, the method only really distinguishes between fluorescing and non-fluorescing material. Since certain materials other than diamonds also fluoresce it can therefore happen that the material deflected from the main stream will contain non-diamond material.

It is an object of the present invention to provide improved apparatus for separating a selected material from a batch of particulate material in which the abovementioned disadvantages have been eliminated or at least minimized.

Apparatus according to the invention comprises means to provide a beam of suitable electromagnetic radiation, means to pulse the beam at a predetermined frequency, means to move a stream of the particulate material through the pulsed beam, a detector for detecting fluorescing material in the stream, and means responsive to the detector to deflect the fluorescing material from the stream.

Further according to the invention the electromagnetic radiation is X-rays provided by an X-ray tube, and the filament of the X-ray tube is pulsed to provide the pulsed beam.

Further according to the invention the beam of electromagnetic radiation is pulsed at a frequency of the order of 1000 pulses per second.

Further according to the invention the duration of each pulse is of the order of five micro-seconds.

Further according to the invention there is provided means to obtain a measure of the decay time of the fluorescence in the fluorescing material after having been pulsed, the deflecting means being responsive to this measure and being adapted to deflect only fluorescing material in the stream having a predetermined decay time.

Suitable radiation for use in practicing the present invention also includes alpha, beta, and gamma radiation.

To illustrate the invention an embodiment thereof is described hereunder with reference to the accompanying drawings in which:

FIG. 1 is a schematic representation of the apparatus of the invention

FIG. 2 is a block schematic diagram of the pulsing system of the invention; and

Figure 3A:
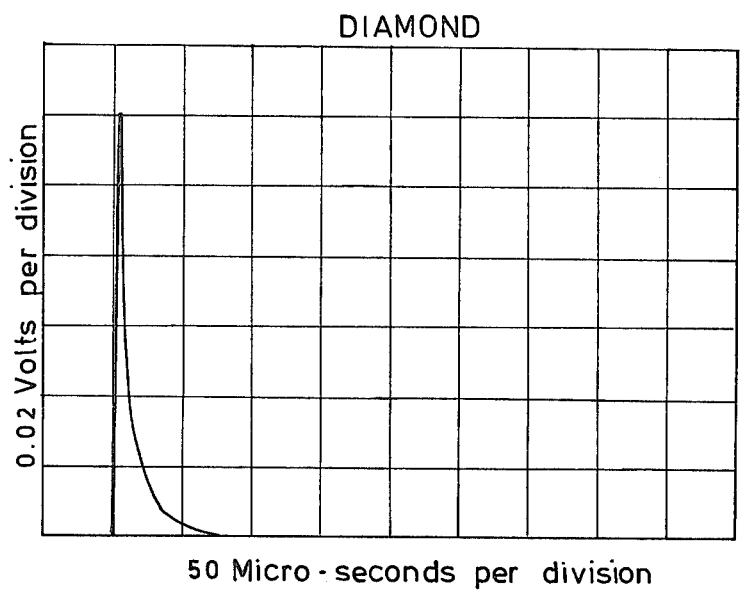
FIGS. 3A and 3B represent the decay times of the fluorescence in respect of Diamond and zircon as measured on an oscilloscope.

With reference to FIG. 1 diamondiferous material 10 is fed from a hopper 12 onto an endless belt 14. The material is discharged from the forward end of the upper bight of the belt in a stream 16.

An X-ray tube 18 having a high emission cathode is arranged close to the end of the belt to irradiate the material in the stream 16.

The filament of the X-ray tube 18 is pulsed at a predetermined frequency by means of a pulser 18A to provide a pulsating beam of X-ray radiation from the tube 18 with which the stream 16 is irradiated. The pulsing frequency is of the order of 1000 pulses per second and the pulse duration is of the order of 5 micro-seconds.

A photomultiplier 20 is located downstream of the X-ray tube 18 but is arranged to focus on the same part of the stream which is irradiated. The photomultiplier 20 is adapted to detect fluorescing material in the stream 16.

A compressed air nozzle 22 is located downstream of the photomultiplier 20 and is arranged to be controlled by the output of the photomultiplier to deflect fluorescing material (such as diamond) from the stream 16.

With reference to FIG. 2 the pulses to the filament of the X-ray tube are obtained by applying mains voltage to a voltage doubler 24 and thereafter to any suitable pulsing circuit 26 the pulsing frequency of which is controlled by a control circuit 28. The pulses are applied to the filament of the X-ray tube 18. A filter 30 is provided to prevent radio frequency pulses from feeding back into the electrical mains.

In one example of the invention the peak voltage of the pulses is 35 Kilovolts and the peak current is 0.5 to 1 Amp.

The average electrical power requirement is of the order of 100 Watts which means that little or no cooling is required on the X-ray tube. In addition, the power supply can be incorporated with the tube, and a separate power supply (and cables) is therefore not necessary. The unit will of course be substantially lighter than the known unit.

The use of a pulsating beam leads to a further significant advantage in that the decay time of the fluorescence in the fluorescing material can be analysed to provide quantitative information on the nature of the fluorescing material detected by the photomultiplier 20. This means that it is therefore possible to distinguish between diamond and other materials which also fluoresce when irradiated with X-rays such as zircon.

Figure 3B:
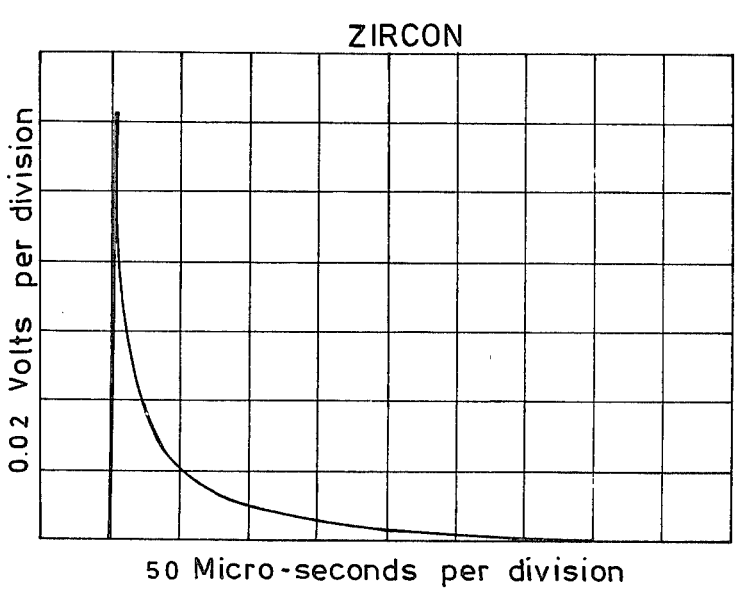

Experiments have for example shown that the decay time of the fluorescence after pulsing is much longer for zircon than for diamond as can be seen from the traces shown in FIG. 3. These traces represent the voltage output of the photomultiplier 20 on the vertical axis against time on the horizontal axis. FIG. 3(a) shows the decay time for diamond whereas FIG. 3(b) shows the decay time for zircon.

By means of a suitable sorting logic circuit 32 therefore the decay times of the various fluorescing materials in the stream 16 can be measured, and the nozzle 22 can be so controlled as to deflect only those materials from the stream which have predetermined decay times. In this manner the nozzle can thus be arranged to deflect only diamond from the stream and none of the other fluorescing materials in the stream.

I claim:

1. Apparatus for separating from a batch of particulate material a selected material having the intrinsic property of fluorescing with a predetermined decay time when irradiated with radiation from a suitable source of radiation, said apparatus comprising means for providing a beam of radiation suitable to cause the selected material to fluoresce with the predetermined decay time; means for pulsing the beam with a repetition interval greater than the predetermined decay time; means for causing a stream of the particulate material to move through the pulsed beam; means for detecting the fluorescing material in the stream and for obtaining a measure of the decay time of the fluorescing; and means responsive to said last-named means for deflecting from the stream only fluorescing material having the predetermined decay time.

2. Apparatus as claimed in claim 1 in which the means for providing a beam comprises an X-ray tube, and in which the means for pulsing the beam pulses the filament of the X-ray tube.

3. Apparatus as claimed in claim 1 in which the means for pulsing the beam pulses the beam at a frequency of the order of 1000 pulses per second.

4. Apparatus as claimed in claim 1 in which the means for pulsing the beam causes pulses of radiation with the duration of each pulse of the order of five microseconds.

5. A method of separating from a batch of particulate material a selected material having the intrinsic property of fluorescing with a predetermined decay time when irradiated with radiation from a suitable source of radiation, said method comprising exposing the particulate material to radiation from a source of the suitable radiation to cause the selected material to fluoresce with the predetermined decay time; pulsing the source of radiation to provide the radiation in pulses having a repetition interval greater than the predetermined decay time; detecting fluorescing material in the particulate material after exposure to the radiation; obtaining a measure of the decay time of the fluorescing; and deflecting from the stream only fluorescing material having the predetermined decay time.

6. A method according to claim 5 wherein the source of radiation is pulsed at a frequency of the order of 1000 pulses per second.

7. A method according to claim 5 wherein the duration of each pulse is of the order of five micro-seconds.

* * * * *